United States Patent
Yu et al.

(10) Patent No.: US 9,272,033 B2
(45) Date of Patent: Mar. 1, 2016

(54) METHODS AND COMPOSITIONS FOR THE PREVENTION AND TREATMENT OF KIDNEY DISEASE

(75) Inventors: Shiguang Yu, Topeka, KS (US); Timothy Arthur Allen, Lawrence, KS (US)

(73) Assignee: HILL'S PET NUTRITION, INC., Topeka, KS (US)

( * ) Notice: Subject to any disclaimer, the term of this patent is extended or adjusted under 35 U.S.C. 154(b) by 2605 days.

(21) Appl. No.: 11/912,085

(22) PCT Filed: Apr. 19, 2006

(86) PCT No.: PCT/US2006/014623
§ 371 (c)(1),
(2), (4) Date: Jun. 30, 2008

(87) PCT Pub. No.: WO2006/113752
PCT Pub. Date: Oct. 26, 2006

(65) Prior Publication Data
US 2008/0287368 A1    Nov. 20, 2008

Related U.S. Application Data

(60) Provisional application No. 60/672,607, filed on Apr. 19, 2005.

(51) Int. Cl.
| *A23K 1/16* | (2006.01) |
|---|---|
| *A61K 45/06* | (2006.01) |
| *A23K 1/18* | (2006.01) |
| *A23L 1/302* | (2006.01) |
| *A23L 1/303* | (2006.01) |
| *A61K 31/015* | (2006.01) |
| *A61K 31/355* | (2006.01) |
| *A61K 31/375* | (2006.01) |

(52) U.S. Cl.
CPC ............... *A61K 45/06* (2013.01); *A23K 1/1603* (2013.01); *A23K 1/1606* (2013.01); *A23K 1/1646* (2013.01); *A23K 1/1846* (2013.01); *A23K 1/1853* (2013.01); *A23L 1/302* (2013.01); *A23L 1/303* (2013.01); *A61K 31/015* (2013.01); *A61K 31/355* (2013.01); *A61K 31/375* (2013.01)

(58) Field of Classification Search
CPC .............................. A61K 45/06; A23K 1/1603
See application file for complete search history.

(56) References Cited

U.S. PATENT DOCUMENTS

| 5,723,441 | A | | 3/1998 | Higley et al. | |
|---|---|---|---|---|---|
| 5,792,473 | A | * | 8/1998 | Gergely et al. | 424/466 |
| 5,851,573 | A | | 12/1998 | Lepine et al. | |
| 6,039,952 | A | | 3/2000 | Sunvold et al. | |
| 6,150,399 | A | * | 11/2000 | Patel et al. | 514/456 |
| 6,306,442 | B1 | | 10/2001 | Sunvold et al. | |
| 6,376,544 | B2 | * | 4/2002 | Lowry et al. | 514/565 |
| 6,447,989 | B1 | | 9/2002 | Comper | |
| 6,458,767 | B1 | | 10/2002 | Murphy-Ullrich et al. | |
| 6,492,325 | B1 | | 12/2002 | Cosgrove | |
| 6,589,748 | B2 | | 7/2003 | Comper | |
| 6,599,876 | B2 | | 7/2003 | Kojima | |
| 6,784,159 | B2 | | 8/2004 | Holub et al. | |
| 2001/0043983 | A1 | | 11/2001 | Hamilton | |
| 2002/0028762 | A1 | | 3/2002 | Kojima | |
| 2003/0060503 | A1 | | 3/2003 | Hamilton | |
| 2003/0105027 | A1 | * | 6/2003 | Rosenbloom | 514/18 |
| 2003/0198661 | A1 | * | 10/2003 | Harper et al. | 424/442 |
| 2004/0047896 | A1 | | 3/2004 | Malno | |
| 2004/0105879 | A1 | | 6/2004 | Heaton et al. | |
| 2004/0137080 | A1 | | 7/2004 | Cremisi | |
| 2005/0026225 | A1 | | 2/2005 | Comper | |

FOREIGN PATENT DOCUMENTS

| CA | 2321909 | 9/1999 |
|---|---|---|
| JP | 2002-535364 | 10/2002 |
| JP | 2004-519241 | 7/2004 |
| WO | 01/58882 A | 8/2001 |
| WO | WO 03/061402 | 7/2003 |
| WO | 2004113570 A2 | 12/2004 |

OTHER PUBLICATIONS

"Metabolic Energy Requirements for Pets Dogs (Dog Daily Calorie Calculator" (http:my cockerspaniel.com/mer.htm); Jul. 2003, pp. 1-3.*
"Hi-Energy Dry Dog Food-Diamond Pet Foods" (http://www.diamondpet.com/products/diamond/dogs/dry_food/diamond_hienergy/); retrieved online on Jul. 17, 2012; pp. 1-2.*
Chen et al. "Vitamin, E selenium, trolox C, ascorbic acid palmitate, acetylcysteine, coenzyme Q, beta-carotene, canthaxanthin, and (=)-catechin protect against oxidative damage to kidney, hear, lung and spleen" Free Radical Research, (1995) pp. 177-186 22:2.
Yu S et al.: "Dietary Supplements of Vitamins E and C and [beta]-Carotene Reduce Oxidative Stress in Cats with Renal Insufficiency" Veterinary Research Communications; An International Journal Publishing Topical Reviews and Research Articles on All Aspects of the Veterinary Sciences, Kluwer Academic Publishers, DO (2006) pp. 403-413 30:4.
European Search Report EP 06 75 8402 mailed Mar. 27, 2009.
Beckman, K. et al., "The Free Radical Theory of Aging Matures," Physiological Reviews (1998) pp. 547-581 78:2.
Cutler, Richard G., "Antioxidants and aging," Am J Clin Nutr (1991) pp. 373S-379S vol. 53.
Tylicki, Leszek et al., "Antioxidants: A Possible Role in Kidney Protection," Kidney Blood Press Research (2003) pp. 303-314 vol. 26.

(Continued)

*Primary Examiner* — Bethany Barham

(57) ABSTRACT

The invention provides compositions for preventing or treating kidney disease comprising vitamin E, vitamin C, and a carotenoid and methods for preventing and treating kidney disease comprising administering such compositions to an animal susceptible to or suffering from kidney disease. In a preferred embodiment, the composition is admixed with one or more food ingredients to produce a food composition useful for preventing or treating kidney disease.

10 Claims, No Drawings

(56) References Cited

OTHER PUBLICATIONS

Ongajoth, Leena, et al. "Role of Lipid Peroxidation, Trace Elements and Antioxidant Enzymes in Chronic Renal Disease Patients," J Med Assoc Thai (1996) pp. 791-800 79:12.

Hasselwander, Oliver, et al. "Oxidative Stress in Chronic Renal Failure," (1998) pp. 1-11,vol. 29.

Shah, Sudhir V., "The Role of Reactive Oxygen Metabolites in Glomerular Disease," Annu. Rev. Physiol. (1995) pp. 245-262, vol. 57.

Kornatowska-Kedzioroa, K. et al., "Effect of Vitamin E and Vitamin C Supplementation on Antioxidative State and Renal Glomerular Basement Membrane Thickness in Diabetic Kidney," Nephron Experimental Nephrology, (2003) pp. 134-e143 vol. 95.

Shiguang et al., "A combination of dietary antioxidant vitamins E, C, and beta-carotene reduces DNA damage in the lymphocytes in cats with naturally occurring renal insufficiency," FASEB meeting on Experimental Biology: Translating the Genome, Washington, D.C., Apr. 17-21, 2004, FASEB Journal 2004, 18(4-5):Abst. 598.8.

American Feed Control Officials, Incorp., Official Publication, 2004, pp. 129-137.

American Feed Control Officials, Incorp., Official publication, p. 220, 2003.

American Feed Control Officials, Incorp., Official publication, pp. 126-140, 2003.

Anonymous, 2004, "Ami-Products—Ingredients" Internet Citation, Retrieved from http://ami.aminews.net/en_ingreidenti.html.

Band et al., Reactive oxygen species: production and role in the kidney, AJP-Renal Physiol., Nov. 1986, 251(5):F765-F776.

Chade et al., "Beneficial Effects of Antioxidant Vitamins on the Stenotic Kidney," Hypertension, 2003, 42:605-612.

Cottrell et al. . Mitochondria and Ageing, Curr Opin Clin. Nutr. Met. Care, (2000) 3:473-478.

Dzanis, 1997, "Selecting Nutritious Pet Foods," Division of Animal Feeds, Center for Veterinary Medicine.

Endraffy et al., The effects of vitamin E on tissue oxidation in nephrotoxic (anti-glomerular basement membrane) nephritis, Pediat. Nephrol. 1991, 3:312-7, abstract only.

Foster et al., Dog Food Standards by the AAFCO, Veterinary Services Dept. http://www.peteducation.com/article.cfm?c=2+1659+1661&aid=662, accessed Sep. 10, 2009.

Greco, 1987, "Dietary Considerations for Dogs with Chronic Renal Failure," Companion Animal Practice, 1(1):54-56, 62.

Hand, 2000, Small Animal Clinical Nutrion, 4th Edition, p. 223.

Jacob et al., "Clinical Evaluation of Dietary Modification for Treatment of Spontaneous Chronic Renal Failure in Dogs," JAVMA, 2002, 220(8):1163-1170.

Jewell et al., "Effect of Increasing Dietary Antioxidants on Concentrations of Vitamin E and Total Alkenals in Serum of Dogs and Cats," Veterinary Therapeutics, 2000, 1(4):264-272.

Klahr et al., "Role of dietary factors in the progression of chronic renal disease," Kidney International, 1983, 24:579-587.

Leibetsedar et al., "Effects of Medium Protein Diets in Dogs with Chronic Renal Failure," J. Nutrition, 1991, 121:S145-S149.

Logham-Adham, 1993, M. "Role of Phosphate Retention in the Progression of Renal Failure," Lab. Clin. Med., 122(1):16-26.

Markwell, "Dietary management of renal failure in the dog and cat," Waltham Focus, 1998, 8(2):16-22.

Mattina, "Analysis of Agricultural Feeds and Pet Foods," 1998, The Connecticut Agricultural Experiment Station, New Haven Bulletin 956, May 1999.

Milgram et al., 2002, "Landmark Discrimination Learning in the Dog: Effects of Age, an Antioxidant Fortified Food and Cognitive Strategy," Neuroscience and Biobehavioral Reviews 26:679-695.

Monzani et al., "LP(A) Levels: Effects of Progressive Chronic Renal Failure and Dietary Manipulation," J of Nephrology, 1997, 10(1):41-45.

Oota, 2004, "Supplementary Effects of Vitamin E of Patients of Kidney Disease," Vitamins (Japan) 78(10):495-512.

Otani, 1998, "Kidney Diseases and Antioxidants," Japanese J. Clin. Nutr. 92(4):381-385.

Pober, "Phosphorous Content in Dog Food," http:www.raingoddess.com/dogfood/phos.html, accessed Dec. 14, 2010.

Polzin et al., 2000, "Dietary Management of Feline Chronic Renal Failure: Where Are We Now? In What Direction Are We Headed?" Journal of Feline Medicine and Surgery, 2:75-82.

Shah, "The Role of Reactive Oxygen Metabolites in Glomerular Disease," Annual Review Physiol., 1995, 57:245-62.

* cited by examiner

METHODS AND COMPOSITIONS FOR THE PREVENTION AND TREATMENT OF KIDNEY DISEASE

CROSS-REFERENCE TO RELATED APPLICATIONS

This application is a National Stage Entry under 35 U.S.C. §371 of International Patent Application No. PCT/US2006/14623, filed Apr. 19, 2006, (now expired), which claims priority to U.S. Provisional Application Ser. No. 60/672,607, filed Apr. 19, 2005, the disclosure of which is incorporated herein by reference.

BACKGROUND OF THE INVENTION

1. Field of the Invention

This invention relates generally to compositions and methods for combating kidney disease and particularly to the use of food compositions for preventing and treating kidney disease.

2. Description of the Prior Art

It has been postulated since 1956 that the production of active oxygen species or free radicals during aerobic respiration results in oxidative damage that hastens aging and death in animals (Beckman, K., et al., "The Free Radical Theory of Aging Matures," Phys. Rev., 78: 547-581 (1998)). Active oxygen species cause aging through various mechanisms, including directly damaging cellular DNA (Cutler, R., "Antioxidants and aging", Am. J. Clin. Nutr., 53: 373S-379S (1991) and lipids and proteins (Tylicki, L., et al. "Antioxidants: A Possible Role in Kidney Protection," Kid. Bl. Press. Res., 26: 303-314 (2003)). Free radicals, often produced in the mitochondria, where aerobic respiration occurs, damage mitochondrial DNA, proteins, and lipids, e.g., U.S. Patent App. Pub. No. US 2003/0060503.

It has also been postulated that active oxygen species may play a role in causing kidney disease (Ongajooth L., et al. "Role of Lipid Peroxidation, Trace Elements and Antioxidant Enzymes in Chronic Renal Disease Patients," J. Med. Assc. Thai., 79:791-800 (1996)). Several mechanisms have been proposed to account for this increase in renal failure, e.g., Hasselwander, et al. "Oxidative Stress in Chronic Renal Failure," Free Rad. Res. 29:1-11 (1998); Shah, S., "The Role of Reactive Oxygen Metabolites in Glomerular Disease," Annu. Rev. Physiol., 57:245-62 (1995)), but scientific studies to date are inconclusive regarding whether antioxidant treatment is beneficial to those with kidney disease. Some studies indicate that there is a role for various antioxidant supplementations in the protection against kidney disease, e.g., Kedziora-Kornatowska et al, "Effect of Vitamin E and Vitamin C Supplementation on Antioxidative State and Renal Glomerular Basement Membrane Thickness in Diabetic Kidney", Nephron Exp. Nephrol., 95:e134-e143 (2003). Other studies note the potential pro-oxidant properties of antioxidant supplements, concluding that there is not yet enough experimental evidence to recommend antioxidant supplements to alleviate kidney disease, e.g., Tylicki, L., et al. However, despite years of studies and developments relating to renal function and kidney disease, kidney disease remains a major health problem. There is, therefore, a need for new methods and compositions for preventing and treating kidney disease.

SUMMARY OF THE INVENTION

It is, therefore, an object of the present invention to provide compositions and methods for preventing and treating kidney disease.

It is another object of the invention to provide food compositions for preventing and treating kidney disease.

It is another object of the invention to provide articles of manufacture in the form of kits that contain combinations of compositions and devices useful for preventing and treating kidney disease.

It is a further object of the invention to decrease the morbidity and mortality caused by kidney disease.

These and other objects are achieved using a novel compositions and methods for preventing or treating kidney disease. The compositions comprise vitamin E, vitamin C, and a carotenoid in amounts sufficient for preventing or treating kidney diseases. Food compositions comprising one or more food ingredients and the compositions are preferred. The methods comprise administering such compositions to patients susceptible to or suffering from kidney disease. Kits comprising the composition components (vitamin E, vitamin C, and a carotenoid) and one or more optional feed ingredients and renal drugs are provided.

Other and further objects, features and advantages of the present invention will be readily apparent to those skilled in the art.

DETAILED DESCRIPTION OF THE INVENTION

Definitions

The term "vitamin E" means any form of vitamin E suitable for consumption by an animal including, but not limited to, any tocopherol or tocotrienol compound, any enantiomer or racemate thereof, and any mixture of such compounds having vitamin E activity, e.g., α-tocopherol (5,7,8-trimethyltocol), β-tocopherol (5,8-dimethyltocol), γ-tocopherol (7,8-dimethyltocol), δ-tocopherol (8-methyltocol), α-tocotrienol (5,7,8-trimethyltocotrienol), β-tocotrienol (5,8-dimethyltocotrienol), γ-tocotrienol (7,8-dimethyltocotrienol), and δ-tocotrienol (8-methyltocotrienol). Vitamin E can be administered as any one or a mixture of the above compounds or in the form of various derivatives thereof such as esters, including vitamin E acetate, succinate, palmitate and the like, that exhibit vitamin E activity after ingestion by a patient. Typically, vitamin E as used in the present invention method comprises α-tocopherol or an ester thereof.

The term "vitamin C" means any form of vitamin C suitable for consumption by an animal including, but not limited to, ascorbic acid, L-ascorbic acid, and various derivatives thereof such as calcium phosphate salt, cholesteryl salt, and ascorbate-2-monophosphate. Salts of vitamin C include the sodium salt, calcium salt, zinc salt, and ferrous salt. Esters include stearate, palmitate and like derivatives. Vitamin C can be in any physical form such as a liquid, a semisolid, a solid, or a heat stable form that exhibits vitamin C activity after ingestion by a patient.

The term "carotenoid" means any form of a carotenoid suitable for consumption by an animal including, but not limited to, natural and synthetic carotenoids derived from orange-yellow pigment in plants, algae, leaves, vegetation, tomato meal, red palm oil, tomato powder, and tomato pomace/pulp. Beta-carotene is a carotenoid precursor of vitamin A occurring naturally in plants.

The term "patient" means a human or other animal likely to develop or suffering from kidney disease, including avian, bovine, canine, equine, feline, hicrine, murine, ovine, and porcine animals. Preferably, the patient is a canine or feline, most preferably a feline.

The term "renal drug" means any compound, composition, or drug useful for preventing or treating kidney disease.

The term "in conjunction" means that one or more of the compositions and compounds (e.g., renal drugs or composition components) of the present invention are administered to a patient (1) together in a food composition or (2) separately at the same or different frequency using the same or different administration routes at about the same time or periodically. "Periodically" means that the compositions, food compositions, and compounds are administered on a dosage schedule acceptable for a specific composition, food composition, and compound and that the food compositions are administered or fed to a patient routinely as appropriate for the particular patient. "About the same time" generally means that the compositions, composition components, renal drugs, and food compositions are administered at the same time or within about 72 hours of each other. In conjunction specifically includes administration schemes wherein renal drugs are administered for a prescribed period and the compositions are administered indefinitely.

The term "antioxidant" means a substance capable of reacting with and neutralizing free radicals. Examples of such substances include beta-carotene, selenium, coenzyme Q10 (ubiquinone), lutein, tocotrienols, soy isoflavones, S-adenosylmethionine, glutathione, N-acetylcysteine, vitamin E, vitamin C, and α-lipoic acid. Examples of foods containing useful levels of one or more antioxidants include but are not limited to *ginkgo biloba*, green tea, broccoli, citrus pulp, grape pomace, tomato pomace, carrot, spinach, and a wide variety of fruit meals and vegetable meals.

This invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise, e.g., reference to "a host cell" includes a plurality of such host cells.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents, patent application, and publications mentioned herein are incorporated herein by reference to the extent allowed by law for the purpose of describing and disclosing the compounds and methodologies reported therein that might be used with the present invention. However, nothing herein is to be construed as an admission that the invention is not entitled to antedate such disclosure by virtue of prior invention.

The Invention

In one aspect, the present invention provides a composition for preventing and treating kidney disease. The composition comprises vitamin E, vitamin C, and a carotenoid in amounts sufficient for preventing or treating kidney disease. The preferred carotenoid is beta-carotene. The invention is based upon the novel discovery that kidney function can be altered by administering the composition to a patient and that altering kidney function with the composition can prevent or treat kidney disease. Without being bound by theory, it is believed that composition if effective in preventing and treating kidney disease because it reduces oxidative stress in a patient.

The composition comprises vitamin E, vitamin C, and a carotenoid in amounts sufficient to administer to a patient at least 30 IU/kg vitamin E, at least 0.01 ppm vitamin C, and at least 0.01 ppm carotenoid. Preferably, the composition comprises from about 30 to about 1,200 IU/kg vitamin E, from about 0.01 to about 350 ppm vitamin C, and from about 0.01 to about 3.5 ppm carotenoid. Most preferably, the composition comprises from about 100 to about 1,000 IU/kg vitamin E, from about 25 to about 250 ppm vitamin C, and from about 0.05 to about 2.5 ppm a carotenoid. The compositions contain vitamin E, vitamin C, and a carotenoid in amounts that are not deleterious to a patient's health, e.g., amounts that do not cause undesirable toxic effects in the patient.

The composition contains vitamin E, vitamin C, and a carotenoid in amounts such that the weight ratio of vitamin C to vitamin E (as DL-alpha-tocopheryl acetate equivalents) is about 10:1 to about 1:1000, preferably about 1:2 to about 1:50 and most preferably about 1:9; the weight ratio of vitamin C to carotenoid is about 2500:1 to about 8:1, preferably about 300:1 to about 20:1 and most preferably about 50:1; and the weight ratio of vitamin E (as DL-alpha-tocopheryl acetate equivalents) to carotenoid is about 13,000:1 to about 170:1, preferably about 2400:1 to about 240:1, and most preferably about 470:1.

In another aspect, the present invention provides a food composition for preventing and treating kidney disease. The food composition comprises one or more food ingredients admixed with vitamin E, vitamin C, and a carotenoid in amounts sufficient for preventing or treating kidney disease. The food composition comprises one or more food ingredients and the vitamin E, vitamin C, and a carotenoid in amounts sufficient to administer to a patient at least 30 IU/kg vitamin E, at least 0.01 ppm vitamin C, and at least 0.01 ppm carotenoid. Preferably, the composition comprises one or more food ingredients and from about 30 to about 1,200 IU/kg vitamin E, from about 0.01 to about 350 ppm vitamin C, and from about 0.01 to about 3.5 ppm carotenoid. Most preferably, the composition comprises one or more food ingredients and from about 100 to about 1,000 IU/kg vitamin E, from about 25 to about 250 ppm vitamin C, and from about 0.05 to about 2.5 ppm carotenoid.

The food ingredients useful in the present invention include any food ingredient suitable for consumption by a patient. Typical food ingredients include but are not limited to fats, carbohydrates, proteins, fibers, and nutritional balancing agents such as e.g., vitamins, minerals, and trace elements. Skilled artisans can select the amount and type of food ingredients for a typical food based upon the dietary requirements of the patient, e.g., the patient's species, age, size, weight, health, and function.

The food ingredient part of the food composition can comprise 100% of any particular food ingredient or can comprise a mixture of food ingredients in various proportions. In preferred embodiments, the food composition comprises a combination of food ingredients in amounts from about 0% to about 50% fat, from about 0% to about 75% carbohydrate, from about 0% to about 95% protein, from about 0% to about 40% dietary fiber, and from about 0% to about 15% of one or more nutritional balancing agents.

The fat and carbohydrate food ingredient is obtained from a variety of sources such as animal fat, fish oil, vegetable oil, meat, meat by-products, grains, other animal or plant sources, and mixtures thereof. Grains include wheat, corn, barley, and rice.

The protein food ingredient is obtained from a variety sources such as plants, animals, or both. Animal protein includes meat, meat by-products, dairy, and eggs. Meats include the flesh from poultry, fish, and animals such as cattle, swine, sheep, goats, and the like, eat by-products include lungs, kidneys, brain, livers, stomachs, and intestines. The protein food ingredient may also be free amino acids and/or peptides. Preferably, the protein food ingredient comprises meat, a meat by-product, dairy products, or eggs.

The fiber food ingredient is obtained from a variety of sources such as vegetable fiber sources, e.g., cellulose, beet pulp, peanut hulls, and soy fiber.

The nutritional balancing agents are obtained from a variety of sources known to skilled artisans, e.g., vitamin and mineral supplements and food ingredients. Vitamins and minerals can be included in amounts required to avoid deficiency and maintain health. These amounts are readily available in the art. The National Research Council (NRC) provides recommended amounts of such nutrients for farm animals. See, e.g., Nutrient Requirements of Swine (10th Rev. Ed., Nat'l Academy Press, Wash. D.C., 1998), Nutrient Requirements of Poultry (9th Rev. Ed., Nat'l Academy Press, Wash. D.C., 1994), Nutrient Requirements of Horses (5th Rev. Ed., Nat'l Academy Press, Wash. D.C., 1989). The American Feed Control Officials (AAFCO) provides recommended amounts of such nutrients for dogs and cats. See American Feed Control Officials, Inc., Official publication, pp. 129-137 (2004). Vitamins generally useful as food additives include vitamin A, vitamin B1, vitamin B2, vitamin B6, vitamin B12, vitamin D, biotin, vitamin K, folic acid, inositol, niacin, and pantothenic acid. Minerals and trace elements useful as food additives include calcium, phosphorus, sodium, potassium, magnesium, copper, zinc, chloride, iron, selenium, iodine, and iron.

The compositions and food compositions may contain additions ingredients such as vitamins, minerals, fillers, palatability enhancers, binding agents, flavors, stabilizers, emulsifiers, sweeteners, colorants, buffers, salts, coatings, and the like known to skilled artisans. Stabilizers include substances that tend to increase the shelf life of the composition such as preservatives, synergists and sequestrants, packaging gases, stabilizers, emulsifiers, thickeners, gelling agents, and humectants. Examples of emulsifiers and/or thickening agents include gelatin, cellulose ethers, starch, starch esters, starch ethers, and modified starches. Specific amounts for each composition component, food ingredient, and other ingredients will depend on a variety of factors such as the particular components and ingredients included in the composition; the species of patient; the patient's age, body weight, general health, sex, and diet; the patient's consumption rate; the type of kidney disease being treated; and the like. Therefore, the component and ingredient amounts may vary widely and may deviate from the preferred proportions described herein.

Food compositions may be prepared in a canned or wet form using conventional food preparation processes known to skilled artisans. Typically, ground animal proteinaceous tissues are mixed with the other ingredients such as fish oils, cereal grains, balancing ingredients, special purpose additives (e.g., vitamin and mineral mixtures, inorganic salts, cellulose and beet pulp, bulking agents, and the like) and water in amounts sufficient for processing. These ingredients are mixed in a vessel suitable for heating while blending the components. Heating of the mixture is effected using any suitable manner, e.g., direct steam injection or using a vessel fitted with a heat exchanger. Following the addition of the last ingredient, the mixture is heated to a temperature of from about 50° F. to about 212° F. Temperatures outside this range are acceptable but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. Sterilization is usually accomplished by heating to temperatures of greater than about 230° F. for an appropriate time depending on the temperature used, the composition, and similar factors. The compositions of the present invention can be added to the food compositions before, during, or after preparation.

Food compositions may be prepared in a dry form using conventional processes known to skilled artisans. Typically, dry ingredients such as animal protein, plant protein, grains, and the like are ground and mixed together. Moist or liquid ingredients, including fats, oils, animal protein, water, and the like are then added to and mixed with the dry mix. The mixture is then processed into kibbles or similar dry pieces. Kibble is often formed using an extrusion process in which the mixture of dry and wet ingredients is subjected to mechanical work at a high pressure and temperature and forced through small openings and cut off into kibble by a rotating knife. The wet kibble is then dried and optionally coated with one or more topical coatings such as flavors, fats, oils, powders, and the like. Kibble also can be made from the dough using a baking process, rather than extrusion, wherein the dough is placed into a mold before dry-heat processing. The food compositions can be in the form of a treat using an extrusion or baking process similar to those described above for dry food. The compositions of the present invention can be added to the food compositions before, during, or after preparation.

Treats include compositions that are given to an animal to entice the animal to eat during a non-meal time, e.g., dog bones for canines. Treats may be nutritional wherein the composition comprises one or more nutrients or and may have a food-like composition. Non-nutritional treats encompass any other treats that are non-toxic. The composition or components are coated onto the treat, incorporated into the treat, or both. Treats of the present invention can be prepared by an extrusion or baking process similar to those used for dry food. Other processes also may be used to either coat the composition on the exterior of existing treat forms or inject the composition into an existing treat form.

All weights and concentrations for the compositions of the present invention are based on dry weight of a composition after all components and ingredients are admixed.

In another aspect, the present invention provides the compositions and food compositions of the present invention further comprising one or more renal drugs. Renal drugs useful in the invention are any renal drugs known to skilled artisans to be useful for combating kidney disease. Preferred drugs include lysosome-activating compounds such as those described in U.S. Patent Number U.S. Pat. No. 6,589,748, triterpene saponins such as those described in U.S. Pat. No. 6,784,159, activin inhibitors such as those described in U.S. Pat. No. 6,599,876 and US Patent Application Number (US-PAN) 20020028762, integrin receptor inhibitors and TGF inhibitors such as those described in U.S. Pat. No. 6,492,325, TGF activation inhibitors such as those described in U.S. Pat. No. 6,458,767, and insulin-like growth factor (IGF) as described in U.S. Pat. No. 5,723,441. Most Preferred drugs include Converting Enzyme (ACE) inhibitors, androgens, erythropoiten, and calcitriol. Angiotensin and endothelin are potent systemic vasoconstrictors with specific intrarenal effects that contribute to progressive renal injury. A variety of renal drugs are used to mitigate the effect of these vasoconstrictors. Angiotensin converting enzyme inhibitors (enalapril—Enacard and Vasotec and benazepril—Lotensin) have been associated with a reduction in the severity of proteinuria and slowing of progression of renal failure. The ACE inhibitor enalapril (Enacard, Vasotec) limits glomerular and systemic hypertension, proteinuria, and glomerular and tubulointerstitial lesions. Angiotensin blockers and endothelin inhibitors have beneficial effects in renal disease. Vasopeptide inhibitors are agents that inhibit both ACE and neutral endopeptidase, an enzyme involved in the breakdown of natriuretic peptides, adrenomedullin, and bradykinin. These renal drugs decrease angiotenin II production and increase accumulation of vasodilators. Renal patients with systemic hypertension respond to calcium channel blockers such as amlodipine (Norvasc). Uremic gastritis (esophagitis, gastritis, gastric ulceration and hemorrhage) is treated with H2 receptor antagonists (cimetidine—Tagamet, famotidine—Pepcid), proton pump blockers (omeprazole—Prilosec), cytoprotective agents (misoprostol—Cytotec), and antiemetic drugs that effect the emetic center (chlorpromazine—Thorazine, perchlorperazine—Compazine, metoclopramide—Reglan). Androgens or anabolic steroids (Stanozol, Winstrol-V) are used in the treatment of anemia associated with chronic renal failure. Hormone replacement therapy using recombinant human (or other species) erythropoiten (Epoetin alpha, Epogen, Procrit) is the treatment of choice for severe anemia associated with renal failure. Phosphate binders (aluminum hydroxide—Amphojel, aluminum carbonate—Basaljel) are used to control hyperphosphatemia and secondary renal hyperparathyroidism. Calcitriol (1,25-dihydroxycholecalciferol) (Rocaltrol) and vitamin D analogues cause a calcium-independent suppression of parathyroid hormone (PTH). Administration of phosphate binders, calcitriol and related compounds has been advocated in chronic renal failure to prevent multi-system toxicity caused by PTH. Potassium depletion and hypokalemia are common in cats with chronic renal failure. Oral supplementation of potassium in the form of potassium gluconate (Tumil K, RenaKare, Kolyum) or citrate is recommended. Holistic renal drugs and compositions are also included in the present invention. Preferred holistic renal drugs include cranberry extract and mannose. Cranberry extract is purported to reduce the prevalence of urinary tract infection which is a common risk factor for long-term decline of renal function. Renal drugs include typical small molecule pharmaceuticals, small proteins, macromolecular proteins and molecules, and antibodies and further include vaccines designed to prevent renal disease. Antibodies include polyclonal and monoclonal antibodies and immunoglobulin fragments such as Fv, Fab, Fab', F(ab')2, or other antigen-binding antibody subsequences that interact with an antigen and perform the same biological function as a native antibody. The renal drugs are administered to the patient using any method appropriate for the renal drug and in amounts known to skilled artisans to be sufficient to treat or prevent renal disease.

In a further aspect, the present invention provides methods for preventing and treating kidney disease. One method comprises administering in conjunction a kidney disease preventing or treating amount of a composition comprising vitamin E, vitamin C, and a carotenoid. In another aspect, the invention provides methods for promoting kidney health by administering a kidney health promoting amount of the composition to a patient. In a further aspect, the invention provides methods for reducing serum urea nitrogen levels in a patient by administering in conjunction a serum urea nitrogen level reducing amount of the composition to a patient. In another aspect, the present invention provides methods for preventing or treating renal insufficiency in a patient by administering in conjunction a renal insufficiency preventing or treating amount of the composition to a patient. The preferred carotenoid is beta-carotene. Other methods for accomplishing these aspects of the invention comprise administering the composition in conjunction with a food composition comprising one or more food ingredients. In a preferred embodiment, the composition and the food ingredients are administered in a food composition comprising an admixture of the composition and the food ingredients. In preferred embodiments, the patient is a feline or a canine.

The compositions are administered to the patient using any suitable method, preferably by feeding the compositions to the patient.

The methods are accomplished by administering the compositions to the patient in various forms. For example, one or more composition components and food ingredients are in separate containers and admixed just prior to administration. In one embodiment, the vitamin E, vitamin C, and a carotenoid are admixed in one container and the resulting composition mixed with food ingredients just prior to administration, e.g., by stirring the composition into or sprinkling the composition onto the food ingredients. In another, one or more of the composition components are admixed with the food ingredients during manufacture and the remaining composition components admixed with such food ingredients just prior to administration. In a further, the composition is a component of a pour-on formulation, preferably containing vitamins and minerals, that is applied to food ingredients prior to administration. In another, the composition is admixed with one or more food ingredients and such admixture is mixed with other food ingredients before administration. In a further, the composition is coated onto the food ingredients during the manufacturing process or after the food composition is manufactured. In another, the composition is administered orally and the food composition is fed to the patient.

The composition is administered orally using any suitable form for oral administration, e.g., tablets, pills, suspensions, solutions (possibly admixed with drinking water), emulsions, capsules, powders, syrups, and palatable feed compositions (a confectionery for a human or a treat or flavored treat for an animal). In a preferred embodiment, the composition components and the food ingredients are admixed during manufacture process used to prepare the food composition suitable for administration in the form of a food for consumption by the patient.

A further method comprises administering the composition or food composition of the present invention in conjunction with one or more renal drugs. Typically, health care professionals, e.g., doctors and veterinarians, diagnose kidney disease in a patient and prescribe a renal drug (any drug useful to prevent or treat kidney disease in a patient) to treat the disease. The patient is administered the renal drug until the symptoms cease and the disease is considered cured. Generally, the renal drug is not administered after the disease is considered cured. Administration of the renal drug is resumed only if the patient has a reoccurrence of the kidney disease. In the present invention, the compositions and renal drugs are administered in conjunction to the patient during treatment. After administration of the renal drug ceases, the compositions are administered to the patient to prevent reoccurrence of the disease. In another embodiment, the compositions are administered to the patient only after use of the renal drug is discontinued to prevent disease reoccurrence.

In a further aspect, the present invention provides a kit for administering a kidney disease preventing or treating composition to a patient comprising in separate containers in a single package at least one of but no more than two of the components of a composition comprising vitamin E, vitamin C, and a carotenoid. For example, the kit could contain three packages with each one containing one of the ingredients. Alternatively, the kit could contain two packages with one containing vitamin E and the other containing vitamin C and a carotenoid. Various combinations of the three components in separate packages are possible. In one embodiment, the kit further comprises one or more food ingredients in a separate package. In this embodiment, the composition or individual composition components are admixed with the food ingredients just prior to administering the resulting admixture to a patient. The kit may also comprise one or more food ingredients containing one or two of the ingredients in one package and a separate package containing the ingredient(s) not contained in the food. Various combinations of the food and the ingredients are possible and can be easily determined by the skilled artisan.

In a further aspect, the present invention provides a kit for administering a kidney disease preventing or treating composition to a patient comprising in separate containers in a single package a composition comprising vitamin E, vitamin C, and a carotenoid and one or more food ingredients in a separate package.

In other embodiments, the kits further comprise one or more renal drugs in a separate package.

In other embodiments, the kits further comprise one or more renal diagnostic devices for determining kidney function and evaluating the presence and severity of kidney disease in a patient in a separate package. The renal diagnostic devices useful in the present invention include any device suitable for determining kidney function and evaluating the presence and severity of kidney disease in a patient. Preferred diagnostic methods include serum urea nitrogen (SUN), creatinine levels, urine specific gravity, and DNA damage, including urine assays for albumin such as those described in U.S. Pat. No. 6,589,748, U.S. Pat. No. 6,447,989 and USPAN 20050026225 and comet trail assays. Diagnostic methods are based upon known techniques including (1) blood markers such as elevated blood urea nitrogen concentration, elevated serum creatinine concentration, hyperphosphatemia, hyperkalemia or hypokalemia, metabolic acidosis and hypoalbuminemia, (2) urine markers such as impaired urine concentrating ability, proteinuria, cylinduria, renal hematuria, inappropriate urine pH, inappropriate urine glucose concentration, and cystinuria, (3) physical, imaging, and diagnostic markers such as size, shape, location, and density, (4) single nucleotide polymorphisms (SNPs) such as those disclosed in WO 2004113570 A2, (5) genetic profiles that are indicative of kidney disease, (6) proteomic profiles that are indicative of kidney disease, and (7) metabolic profiles that are indicative of kidney disease. These diagnostic methods and devices (e.g., test strips, ELISA assays, comet assays,) based upon such methods are commonly available to skilled artisans such as scientists and health care professionals and many are available to consumers, e.g., the Heska Corporation's (Fort Collins Colo.) E.R.D.—HealthScreen Urine Tests that detects small amounts of albumin in the urine ("microalbuminuria").

The kits further comprise information that the use of the compositions of the present invention will prevent or treat kidney disease.

The kits contain the composition components in amounts sufficient to supply to a patient at least 30 IU/kg vitamin E, at least 0.01 ppm vitamin C, and at least 0.01 ppm carotenoid.

The kits of the present invention contain the compositions, composition components, food compositions, food ingredients, renal drugs, and renal diagnostic devices in any of various combinations. For example, one kit comprises a food composition comprising an admixture of one or more food ingredients and the composition in combination with a renal diagnostic device or a renal drug or both. Another kit contains the composition components in separate packages and one or more food ingredients in one or more separate packages with or without renal drugs or renal diagnostic devices in separate packages. Numerous such combinations can be constructed by the skilled artisan.

In another aspect, the present invention provides a means for communicating information about or instructions for admixing and administering one or more of the compositions, composition components, food compositions, food ingredients, and renal drugs and information about or instructions for using the renal diagnostic devices of the present invention. The communicating means comprises a document, digital storage media, optical storage media, audio presentation, or visual display containing the information or instructions. Preferably, the communication is a displayed web site or a brochure, product label, package insert, advertisement, or visual display containing such information or instructions. Useful information includes one or more of (1) methods and techniques for combining and administering the compositions, composition components, food compositions, food ingredients, and renal drugs, (2) information for using the renal diagnostic devices, (3) details about the side effects, if any, caused by using the present invention in combination with other drugs, and (4) contact information for patients to use if they have a question about the invention and its use. Useful instructions include dosages, administration amounts and frequency, and administration routes. The communication means is useful for instructing a patient on the benefits of using the present invention and communicating the approved methods for administering the invention to a patient.

In a further aspect, the present invention provides for a use of a composition comprising vitamin E, vitamin C, and a carotenoid to prepare a medicament. In another, the invention provides for the use of such composition to prepare a medicament for preventing or treating kidney disease. Generally, medicaments are prepared by admixing a compound or composition with excipients, buffers, binders, plasticizers, colorants, diluents, compressing agents, lubricants, flavorants, moistening agents, and other ingredients known to skilled artisans to be useful for producing medicaments and formulating medicaments that are suitable for administration to an animal.

The compositions, methods, and kits are useful for decreasing the morbidity and mortality for patients susceptible to or suffering from kidney disease.

EXAMPLES

This invention can be further illustrated by the following examples of preferred embodiments thereof, although it will be understood that these examples are included merely for purposes of illustration and are not intended to limit the scope of the invention unless otherwise specifically indicated.

Measuring Kidney Function and Evaluating Kidney Disease

The kidney's primary function is to remove metabolic waste or toxins from the blood. Enhanced or improved kidney function refers to a relative increase in the kidneys' ability to remove waste or toxins from the blood. Conversely, impaired or decreased kidney function refers to a relative decrease in the kidneys' ability to remove waste or toxins from the blood.

There are several reliable methods for determining kidney function and evaluating kidney disease, i.e., serum urea nitrogen (SUN), creatinine levels, urine specific gravity, and DNA damage.

Serum urea nitrogen (SUN): Urea is a waste product of protein and/or amino acid metabolism that is removed from the blood by the kidneys. When a patient is experiencing reduced kidney function, SUN levels increase over time because damage to the kidney lessens the kidney's ability to adequately filter the urea and remove it from the blood. Thus, relative kidney function can be determined by comparing the patient's SUN level over time. If the SUN level increases over time, kidney function is decreasing. If the SUN level decreases over time, the kidney function is improving.

Creatinine Levels: Creatinine is removed from the blood by the kidneys. When a patient is experiencing reduced kidney function, creatinine levels increase over time because damage to the kidney lessens the kidney's ability to adequately filter the creatinine and remove it from the blood. Thus, relative kidney function can be determined by comparing the patient's creatinine level over time. If the creatinine level increases over time, kidney function is decreasing. If the creatinine level decreases over time, the kidney function is improving.

Urine Specific Gravity: The urine specific gravity is a measure of the concentration of the urine. The specific gravity of water is 1.000. A dilute urine sample has a specific gravity less than 1.025, often less than 1.010. A concentrated urine sample has a specific gravity greater than 1.030, often greater than 1.040. A more concentrated urine sample indicates that the kidneys are doing a more effective job of removing waste and toxins from the blood. Thus, relative kidney function can be determined by comparing the patient's urine specific gravity over time. If the urine specific gravity increases over time, kidney function is increasing. If the urine specific gravity decreases over time, kidney function is decreasing.

DNA Damage: The presence and severity of DNA damage in a cell can be measured in a number of ways, including the single cell gel electrophoresis assay known as the "comet assay." In a comet assay, cells are embedded in a thin agarose gel on a microscope slide. Subsequently, the cells are lysed. The DNA is then allowed to unwind under alkaline or neutral conditions. After the DNA has unwound, it is electrophoresed and stained with a fluorescent dye. During electrophoresis, damaged DNA (DNA fragments) migrates away from the nucleus. The extent of DNA released from the head of the comet is directly proportional to the amount of DNA damage in the cell. There are several measurements that are used in conjunction with the comet assay to quantify the presence and severity of DNA damage. "Head DNA" is a measurement, in percent, of the DNA that is present in the head of the comet. "Tail DNA" is a percentage of the DNA that is present in the tail of the comet. A relative increase in head DNA, and a consequent decrease in tail DNA, means that DNA damage is decreasing. "Tail length" is the distance of DNA migration from the body of the nuclear core and it is used to evaluate the extent of DNA damage. A relative increase in tail length means that DNA damage is increasing. "Tail moment" is defined as the product of the tail length and the fraction of total DNA in the tail. Tail moment incorporates a measure of both the smallest detectable size of migrating DNA (reflected in the comet tail length) and the number of relaxed or/broken pieces (represented by the intensity of DNA in the tail). A relative increase in tail moment means that DNA damage is increasing. The presence and severity of DNA oxidative damage can also be detected by measuring the presence of serum 8-hydroxy-2'-deoxyguanosine (8-OHdG). 8-OHdG is a DNA nucleotide that is found in blood serum. A relative increase in the amount of 8-OHdG correlates to an increase in DNA oxidation and, as such, DNA damage. Conversely, a relative decrease in the amount of 8-OHdG correlates to a decrease in DNA oxidation and DNA damage.

Example 1

A study was conducted to investigate the status of oxidative stress in cats with chronic renal insufficiency and to determine if the compositions of the present invention have any beneficial effect for preventing or treating kidney disease, including determining whether the composition reduce the serum urea nitrogen concentration and oxidative stress as measured by DNA damage in the studied cats.

Ten cats with renal insufficiency (renal cats) were identified based on serum urea nitrogen, serum creatinine, and urine specific gravity. Ten non-renal cats were also identified as healthy cats. The healthy cats were paired with the renal cats in breed, age, and gender. Compared to the healthy cats, the renal cats had significantly and abnormally elevated serum urea nitrogen and creatinine, and decreased urine specific gravity. Renal cats also had elevated DNA damage as indicated by increased serum 8-OHdG concentration and reduced Head DNA of Comet Assay.

All of the cats were fed a dry, commercial feline food composition comprising brewer's rice, corn gluten meal, egg, chicken, fish, fiber, calcium carbonate, potassium chloride, potassium citrate, choline chloride, methionine, iodized salt, taurine, calcium sulfate dehydrate, ethoxyquin, animal fat, flavors, L-tryptophan, vitamin mixtures, and mineral mixtures for four weeks (Diet I). All of the cats were then fed the same diet supplemented with a package of antioxidants (vitamin E, vitamin C, and a carotenoid) for another four weeks (Diet II). All cats were fed a daily amount of food that was adjusted to maintain their body weight, and had free access to tap water.

Diet I contained about 0 ppm vitamin C, about 166 IU/kg vitamin E, and about 2.3 IU/kg carotenoid. Diet II contained about 84 ppm of vitamin C, about 741 IU/kg vitamin E, and about 3.5 IU/kg carotenoid.

Blood samples from all cats were taken in weeks 4 and 8 and analyzed for serum urea nitrogen, serum creatinine, serum 8-OhdG, and DNA damage. The urine specific gravity was also measured and calculated. The results are shown in Table 1.

TABLE 1

Measurements of Serum Urea Nitrogen, Serum Creatinine, Urine Specific Gravity, and DNA Damage

| Measurement | Week 4 (Diet I) | | Week 8 (Diet II) | |
| --- | --- | --- | --- | --- |
| | Renal Cats | Healthy Cats | Renal Cats | Healthy Cats |
| Serum Urea Nitrogen (mg/dl) | 40.1 | 26.9 | 34.5* | 25.1 |
| Serum Creatinine (mg/dl) | 1.9 | 1.4 | 1.8 | 1.3 |
| Urine Specific Gravity | 1.027 | 1.044 | 1.029 | 1.044 |
| Serum 8-OHdG (ng/ml) | 776 | 385 | 31* | 33 |
| Comet Assay | | | | |
| Head DNA (%) | 66.7 | 73 | 80.3* | 81.8* |
| Tail DNA (%) | 33.3 | 27 | 19.7* | 18.3* |
| Tail Moment | 39.1 | 27.5 | 7.3* | 5.4* |
| Tail Length (μm) | 82.9 | 71.9 | 23.2* | 18.4* |

*Significantly differs from Diet I

Referring to Table 1, the results show that the SUN in renal cats decreased significantly after the cats were fed the compositions of the present invention. Therefore, renal cats showed significant improved kidney function in response to a diet containing the composition of the present invention, i.e., vitamin E, vitamin C, and a carotenoid. Conversely, the healthy cats did not show a significant change in SUN levels. Further, the results show that cell DNA damage in renal cats decreased significantly after the cats were fed the compositions of the present invention. More particularly, the results show that all four comet assay parameters indicate a significant decrease in DNA damage. Similarly, a significant decrease in S—OHdG also indicates a significant decrease in DNA oxidation and DNA damage. These results show that the compositions of the present invention can be used to prevent or treat kidney disease in cats suffering from kidney disease, in the form of renal insufficiency or renal failure.

In the specification, there have been disclosed typical preferred embodiments of the invention and, although specific terms are employed, they are used in a generic and descriptive sense only and not for purposes of limitation, the scope of the invention being set forth in the following claims. Obviously many modifications and variations of the present invention are possible in light of the above teachings. It is therefore to be understood that within the scope of the appended claims the invention may be practiced otherwise than as specifically described.

What is claimed is:

1. A food composition comprising vitamin E, vitamin C, and a carotenoid in amounts sufficient for preventing or treating kidney disease, wherein the vitamin E is in an amount of from about 30 to about 1200 IU/kg, the vitamin C is in an amount of from about 0.01 to about 350 ppm vitamin C, and the carotenoid is in an amount from about 0.01 to about 3.5 ppm.

2. The composition of claim 1 comprising vitamin E, vitamin C, and a carotenoid in amounts sufficient to administer to a patient from at least 30 to 1200 IU/kg vitamin E, from at least 0.01 to 350 ppm vitamin C, and from at least 0.01 to 350 ppm carotenoid, wherein the patient is a canine or a feline.

3. The composition of claim 1 wherein the carotenoid is beta-carotene.

4. The composition of claim 1 further comprising one or more renal drugs.

5. The composition of claim 4 wherein the renal drug is selected from the group consisting of Converting Enzyme (ACE) inhibitors, androgens, erythropoietin, angiotensin, endothelin, angiotensin converting enzyme inhibitors, calcium channel blockers, H2 receptor antagonists, proton pump blockers, and calcitrol.

6. The composition of claim 1 further comprising one or more food ingredients.

7. The composition of claim 6 wherein the food ingredient is selected from the group consisting of fats, carbohydrates, proteins, fibers, and nutritional balancing agents.

8. The composition of claim 6 containing food ingredients in amounts from about 2% to about 50% fat, from about 0% to about 75% carbohydrate, from about 0% to about 95% protein, from about 0% to about 40% dietary fiber, and from about 0% to about 15% of one or more nutritional balancing agents.

9. The composition of claim 6 further comprising one or more renal drugs.

10. The composition of claim 9 wherein the renal drug is selected from the group consisting of Converting Enzyme (ACE) inhibitors, androgens, erythropoietin, angiotensin, endothelin, angiotensin converting enzyme inhibitors, calcium channel blockers, H2 receptor antagonists, proton pump blockers, and calcitrol.

* * * * *